(12) United States Patent
Mostowfi

(10) Patent No.: US 8,485,026 B2
(45) Date of Patent: Jul. 16, 2013

(54) MICROFLUIDIC METHOD FOR MEASURING THERMO-PHYSICAL PROPERTIES OF A RESERVOIR FLUID

(75) Inventor: Farshid Mostowfi, Edmonton (CA)

(73) Assignee: Schlumberger Technology Corporation, Sugar Land, TX (US)

(*) Notice: Subject to any disclaimer, the term of this patent is extended or adjusted under 35 U.S.C. 154(b) by 348 days.

(21) Appl. No.: 12/867,444

(22) PCT Filed: Feb. 7, 2009

(86) PCT No.: PCT/IB2009/050500
§ 371 (c)(1),
(2), (4) Date: Sep. 27, 2010

(87) PCT Pub. No.: WO2009/109868
PCT Pub. Date: Sep. 11, 2009

(65) Prior Publication Data
US 2011/0030466 A1 Feb. 10, 2011

(30) Foreign Application Priority Data
Mar. 3, 2008 (CA) ..................................... 2623793

(51) Int. Cl.
*E21B 49/00* (2006.01)
*G01N 7/00* (2006.01)
*G01N 1/00* (2006.01)

(52) U.S. Cl.
USPC ...................... 73/152.23; 73/64.44; 73/64.56

(58) Field of Classification Search
USPC ........... 73/61.41, 61.46, 64.44, 64.56, 152.23
See application file for complete search history.

(56) References Cited

U.S. PATENT DOCUMENTS

| | | | |
|---|---|---|---|
| 6,543,274 B1 | 4/2003 | Herrmann et al. | |
| 6,758,090 B2 * | 7/2004 | Bostrom et al. | 73/152.58 |
| 6,911,894 B2 * | 6/2005 | Bonne et al. | 338/25 |
| 2002/0083771 A1 * | 7/2002 | Khuri-Yakub et al. | 73/589 |
| 2004/0098202 A1 | 5/2004 | McNeil, III et al. | |
| 2005/0052509 A1 | 3/2005 | Gilligan et al. | |
| 2005/0161327 A1 | 7/2005 | Palmieri | |
| 2006/0008382 A1 | 1/2006 | Salamitou et al. | |
| 2006/0008913 A1 | 1/2006 | Angelescu et al. | |
| 2011/0259090 A1 * | 10/2011 | Angelescu et al. | 73/64.56 |

FOREIGN PATENT DOCUMENTS

| | | |
|---|---|---|
| RU | 2267092 C2 | 12/2005 |
| WO | 2005124257 A1 | 12/2005 |

OTHER PUBLICATIONS

Grant Notice of Russian Application Serial No. 2010140426 dated Feb. 2, 2012.
Harrison, D. Jed, et al, Micromachining a Miniaturized Capillary Electrophoresis-Based Chemical Analysis System on a Chip, Science, vol. 261, Aug. 13, 1993, pp. 895-897.

(Continued)

*Primary Examiner* — Hezron E Williams
*Assistant Examiner* — Nathaniel Kolb
(74) *Attorney, Agent, or Firm* — Daren C. Davis; Wayne I. Kanak

(57) ABSTRACT

A method of measuring thermo-physical properties of a reservoir fluid includes introducing the fluid under pressure into a microchannel, establishing a stabilized flow of the fluid through the microchannel, inducing bubble formation in the fluid disposed in the microchannel, and determining the thermo-physical properties of the fluid based upon the bubbles formed as the fluid flows through the microchannel.

5 Claims, 5 Drawing Sheets

OTHER PUBLICATIONS

Kuo, Chih-Jung, et al, Bubble Dynamics During Boiling in Enhanced Surface Microchannels, Journal of Microelectromechanical Systms, vol. 15, No. 6, Dec. 2006, pp. 1514-1527.

Bowden, S.A. et al, The Liquid-Liquid Diffusive Extraction of Hydrocarbons from a North Sea Oil Using a Microfluidic Format, www.rsc.org/loc, Lab on a Chip, Accepted Apr. 5, 2006, First published as an Advance Article on the web Apr. 13, 2006, DOI: 10.1039/bt18162c, pp. 740-743.

Kim, Dong Sung, et al, A Serpentine Laminating Micromixer Combining Splitting/recombination and Advection, Accepted Mar. 24, 2005, First published as an Advance Article on the web Apr. 26, 2005 DOI:10.1039/b418314b www.rsc.org/loc, Lab on a Chip pp. 739-747.

Steinke, Mark E. et al, Single-Phase Heat Transfer Enhancement Techniques in Microchannel and Minichannel Flows, Microchannels and Minichannels—2004, Jun. 17-19, 2004, Rochester, New York, USA by ASME ICMM2004-2328, pp. 141-148.

Verpoorte, Elisabeth et al, Microfluidics Meets MEMS, Proceedings of the IEEE, vol. 91, No. 6, Jun. 2003, pp. 930-953.

* cited by examiner

MICROFLUIDIC METHOD FOR MEASURING THERMO-PHYSICAL PROPERTIES OF A RESERVOIR FLUID

BACKGROUND OF THE INVENTION

1. Field of the Invention

The present invention relates to an apparatus and method for measuring thermo-physical properties of a reservoir fluid.

2. Description of Related Art

The measurement of reservoir fluid properties is a key step in the planning and development of a potential oilfield. It is often desirable to perform such measurements frequently on a producing well to provide an indication of the performance and behavior of the production process. Examples of such measurements are pressure, volume, and temperature measurements, often referred to as "PVT" measurements, which are instrumental in predicting complicated thermo-physical behavior of reservoir fluids. One important use of PVT measurements is the construction of an equation of state describing the state of oil in the reservoir fluid. Other properties of interest that may be determined using PVT measurements include fluid viscosity, density, chemical composition, gas-oil-ratio, and the like. Once a PVT analysis is complete, the equation of state and other parameters can be input into reservoir modeling software to predict the behavior of the oilfield formation.

Conventional PVT measurements are performed using a cylinder containing the reservoir fluid. A piston disposed in the cylinder maintains the desired pressure on the fluid, while the heights of the liquid and gaseous phases are measured using, for example, a cathetometer.

Despite wide application, conventional PVT measurements suffer from several significant limitations. Firstly, a conventional PVT analysis typically requires up to a few weeks to complete. Furthermore, a substantial volume of reservoir fluid, often as much as 4 liters, must be maintained at pressures up to about 1400 kilograms/square centimeter (20,000 pounds/square inch) from the wellsite to the testing laboratory. Shipping and handling such a large sample at these high pressures is costly and poses considerable safety issues.

While there are ways of characterizing properties of reservoir fluid known in the art, considerable shortcomings remain.

BRIEF SUMMARY OF THE INVENTION

There is a need for a microfluidic apparatus and method for measuring thermo-physical properties of a reservoir fluid.

Therefore, it is an object of the present invention to provide a microfluidic apparatus and method for measuring thermo-physical properties of a reservoir fluid.

In one aspect, a microfluidic apparatus for measuring thermo-physical properties of a reservoir fluid is provided. The apparatus includes a first substrate defining a microchannel, an entrance well, and an exit well. The microchannel extends between and is in fluid communication with the entrance well and the exit well. The apparatus further includes a second substrate attached to the first substrate to form a microfluidic device. The second substrate defines an entrance passageway in fluid communication with the entrance well and an exit passageway in fluid communication with the exit well. The entrance passageway is configured to receive the reservoir fluid under pressure.

In another aspect, a method for measuring thermo-physical properties of a reservoir fluid is provided. The method includes providing a microfluidic device defining a fluid entrance, a fluid exit, and a microchannel extending between and in fluid communication with the fluid entrance and the fluid exit. The method further includes introducing the reservoir fluid under pressure into the microchannel via the fluid entrance and establishing a stabilized flow of the reservoir fluid through the microchannel and from the fluid exit. The method further includes determining one or more thermo-physical properties of the reservoir fluid based upon the size of bubbles formed in the reservoir fluid disposed in the microchannel and a concentration of bubbles in the reservoir fluid disposed in the microchannel.

The present invention provides significant advantages, including: (1) providing a way to measure thermo-physical properties of a reservoir fluid with small amounts of reservoir fluid; (2) providing a way to perform pressure-volume-temperature analyses of a reservoir fluid in a timely fashion; and (3) providing a way to measure thermo-physical properties of a reservoir fluid using image analysis.

Additional objectives, features, and advantages will be apparent in the written description which follows.

BRIEF DESCRIPTION OF THE DRAWINGS

The novel features of the invention are set forth in the appended claims. However, the invention itself, as well as a preferred mode of use, and further objectives and advantages thereof, will best be understood by reference to the following detailed description when read in conjunction with the accompanying drawings, wherein:

Figure 1:
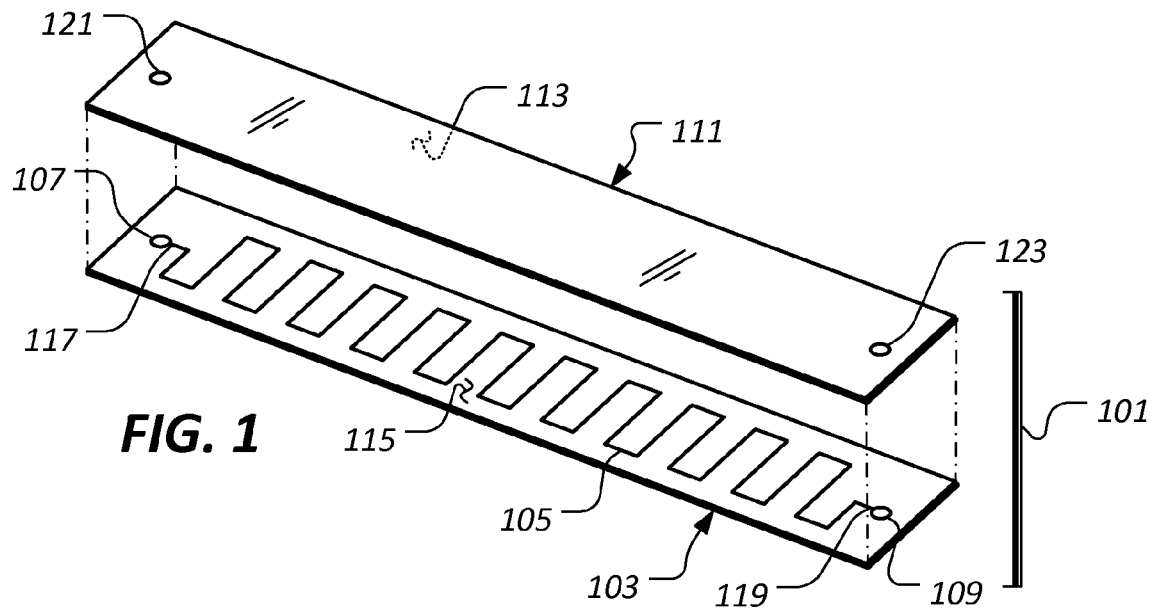
FIG. 1 is a stylized, exploded, perspective view of a first illustrative embodiment of a microfluidic device for measuring thermo-physical properties of a reservoir fluid.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the scope of the invention as defined by the appended claims.

DETAILED DESCRIPTION OF THE INVENTION

Illustrative embodiments of the invention are described below. In the interest of clarity, not all features of an actual implementation are described in this specification. It will be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

The present invention represents a microfluidic apparatus and method for measuring thermo-physical properties of a reservoir fluid. For the purposes of this disclosure, the term "reservoir fluid" means a fluid stored in or transmitted from a subsurface body of permeable rock. Moreover, for the purposes of this disclosure, the term "microfluidic" means having a fluid-carrying channel exhibiting a width within a range of tens to hundreds of micrometers, but exhibiting a length that is many times longer than the width of the channel.

FIG. 1 depicts a stylized, exploded, perspective view of a first illustrative embodiment of a microfluidic device 101. In the illustrated embodiment, microfluidic device 101 comprises a first substrate 103 defining a microchannel 105, an entrance well 107 and an exit well 109. Microchannel 105 extends between and is in fluid communication with entrance well 107 and exit well 109. Microchannel 105 forms a serpentine pattern in first substrate 103, thus allowing microchannel 105 to extend a significant length but occupy a relatively small area. In a preferred embodiment, microchannel 105 exhibits a length of one or more meters, a width of about 100 micrometers, and a depth of about 50 micrometers, although the present invention also contemplates other dimensions for microchannel 105. Microfluidic device 101 further comprises a second substrate 111 having a lower surface 113 that is bonded to an upper surface 115 of first substrate 103. When second substrate 111 is bonded to first substrate 103, microchannel 105 is sealed except for an inlet 117 at entrance well 107 and an outlet 119 at exit well 109. Second substrate 111 defines an entrance passageway 121 and an exit passageway 123 therethrough, which are in fluid communication with entrance well 107 and exit well 109, respectively, of first substrate 103.

In FIG. 1, first substrate 103 is preferably made of silicon and is approximately 500 micrometers thick, and second substrate 111 is made of glass, such as borosilicate glass, although the present invention contemplates other materials for first substrate 103, as is discussed in greater detail herein. Exemplary borosilicate glasses are manufactured by Schott North America, Inc. of Elmsford, N.Y., USA, and by Corning Incorporated of Corning, N.Y., USA.

In operation, pressurized reservoir fluid is urged through entrance passageway 121, entrance well 107, and inlet 117 into microchannel 105. The reservoir fluid exits microchannel 105 through outlet 119, exit well 109, and exit passageway 123. Microchannel 105 provides substantial resistance to the flow of reservoir fluid therethrough because microchannel 105 is very small in cross-section in relation to the length of microchannel 105. When fluid flow is established between inlet 117 and outlet 119 of microchannel 105, the pressure of the reservoir fluid within microchannel 105 drops from an input pressure, e.g., reservoir pressure, at inlet 117 to an output pressure, e.g., atmospheric pressure, at outlet 119. The overall pressure drop between inlet 117 and outlet 119 depends upon the inlet pressure and the viscosity of the reservoir fluid. Fluid flow through microchannel 105 is laminar and, thus the pressure drop between inlet 117 and outlet 119 is linear when the reservoir fluid exhibits single-phase flow.

Figure 2:
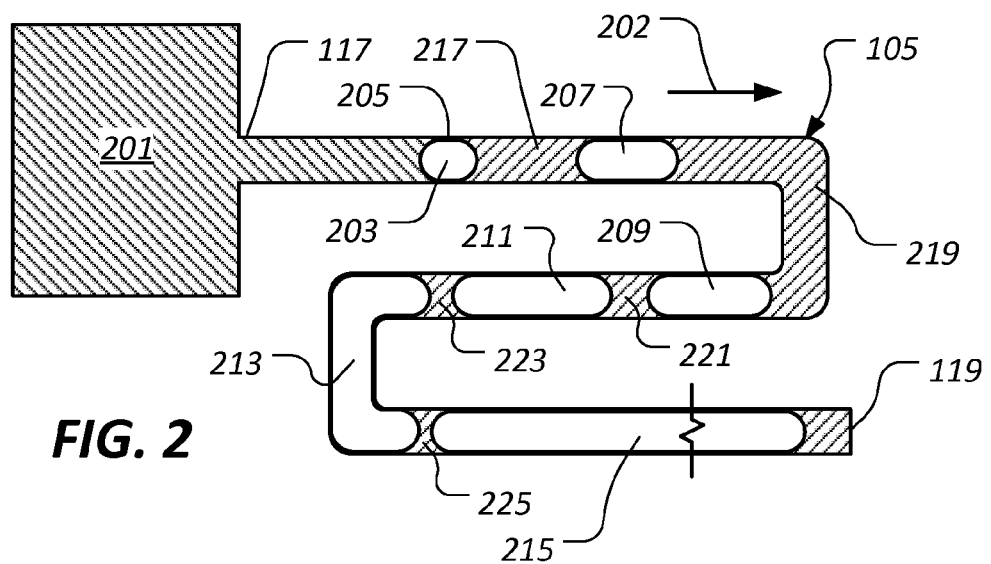
FIG. 2 is a stylized, schematic representation of a reaction of reservoir fluid as the reservoir fluid flows through the microfluidic device of FIG. 1.

FIG. 2 provides a stylized, schematic representation of the reaction of reservoir fluid 201 as the reservoir fluid flows through microchannel 105 in a direction generally corresponding to arrow 202. When the reservoir fluid enters inlet 117 of microchannel 105, the reservoir fluid is at a pressure above the "bubble point pressure" of the reservoir fluid. The bubble point pressure of a fluid is the pressure at or below which the fluid begins to boil, i.e., bubble, at a given temperature. When the reservoir fluid exits outlet 119 of microchannel 105, the reservoir fluid is at a pressure below the bubble point pressure of the reservoir fluid. Thus, a "first" bubble 203 forms in the reservoir fluid at some location, e.g., at 205 in FIG. 2, within microchannel 105 where the reservoir fluid is at the bubble point pressure. Downstream of location 205, multi-phase flow, e.g., gas and liquid flow, of reservoir fluid 201 occurs in microchannel 105. Previously-formed bubbles, e.g. bubbles 207, 209, 211, 213, 215, and the like, grow in size as reservoir fluid 201 flows within microchannel 105 beyond the location corresponding to the formation of the first bubble due to decreased pressure in this portion of microchannel 105 and more evaporation of the lighter components of reservoir fluid 201. The bubbles are separated by slugs of liquid, such as slugs 217, 219, 221, 223, 225, and the like. Expansion of the bubbles, such as bubbles 207, 209, 211, 213, 215, results in an increased flow velocity of the bubbles and liquid slugs, such as slugs 217, 219, 221, 223, 225, within microchannel 105. The mass flow rate of reservoir fluid 201 is substantially constant along microchannel 105; however, the volume flow rate of reservoir fluid 201 increases as reservoir fluid flows along microchannel 105.

Figure 3:
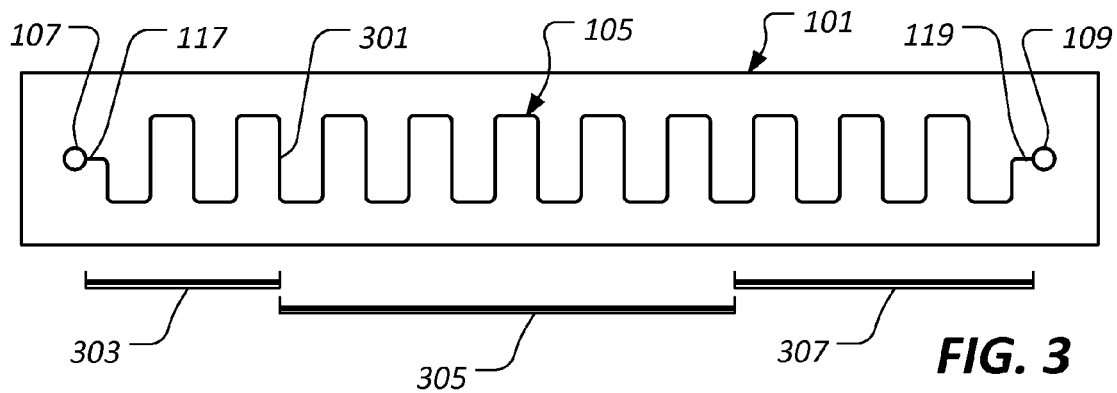
FIG. 3 is a top, plan view of the microfluidic device of FIG. 1 depicting three reservoir fluid flow regimes.

Thermo-physical properties of the reservoir fluid, such as reservoir fluid 201 of FIG. 2, for example gas-oil-ratio, phase envelope, and equation of state, can be determined by measuring the size and concentration of bubbles within microchannel 105. Referring now to FIG. 3, the flow of the reservoir fluid through microchannel 105 is depicted in three regimes. A first bubble, such as first bubble 203 of FIG. 2, is formed at 301 along microchannel 105. From inlet 117 of microchannel 105 to location 301 of the first bubble, indicated in FIG. 3 as a first region 303, the pressure of the reservoir fluid is above the bubble point. No bubbles are observed within first region 303. In first region 303, the flow of the reservoir fluid is substantially laminar due to a low Reynolds number and the pressure drops substantially linearly therein. Once bubbles are formed, the bubbles move along within microchannel 105 toward outlet 119 and the volumes of the bubbles increases. In a second region 305, the void fraction, i.e., the volume of gas to total volume, of the reservoir fluid is less than one. In a third region 307, the flow of the reservoir fluid is dominated by high-speed gas flow. The gas bubbles are separated by small droplets of liquid, such as water. The pressure of the reservoir fluid within third region 307 decreases rapidly. Gas bubbles flow within second region 305 at a slower rate than in third region 307, where they are often nearly impossible to follow with the naked eye.

Figure 4:
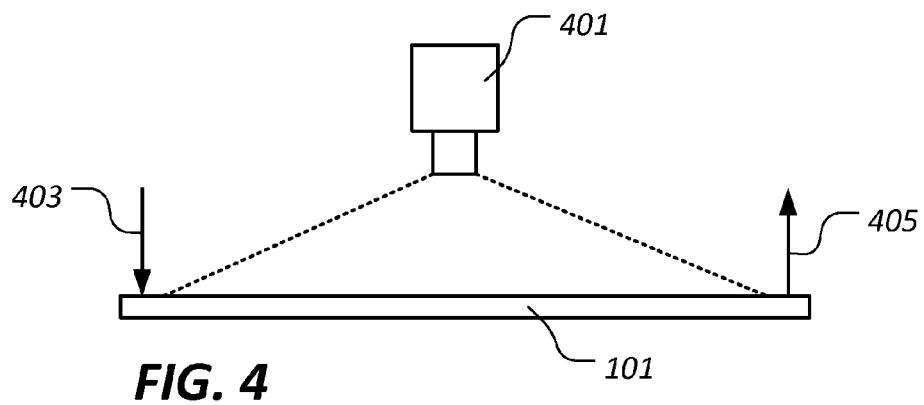
FIG. 4 is a stylized, side, elevational view of a reservoir fluid measurement system, including the microfluidic device of FIG. 1 and a camera for generating images of the microfluidic device in use.

Once a stabilized flow of reservoir fluid is established in microchannel 105, a camera 401 is used to capture snapshots of the flow, as shown in FIG. 4. Note that the flow of reservoir fluid into inlet 117 (shown in FIGS. 1 and 3) is represented by an arrow 403 and that the flow of reservoir fluid from outlet 119 (shown in FIGS. 1 and 3) is represented by an arrow 405. In one embodiment, camera 401 is a charge-coupled device (CCD) type camera. The images produced by camera 401 are processed using image analysis software, such as ImageJ 1.38x, available from the United States National Institutes of Health, of Bethesda, Md., USA, and ProAnalyst, available from Xcitex, Inc. of Cambridge, Mass., USA, to measure the size and concentration of the bubbles in the reservoir fluid disposed in microchannel 105. Using this technique, many thermo-physical properties of the reservoir fluid, such as gas-oil-ratio, phase envelope, and equation of state, can be determined.

Figure 5:
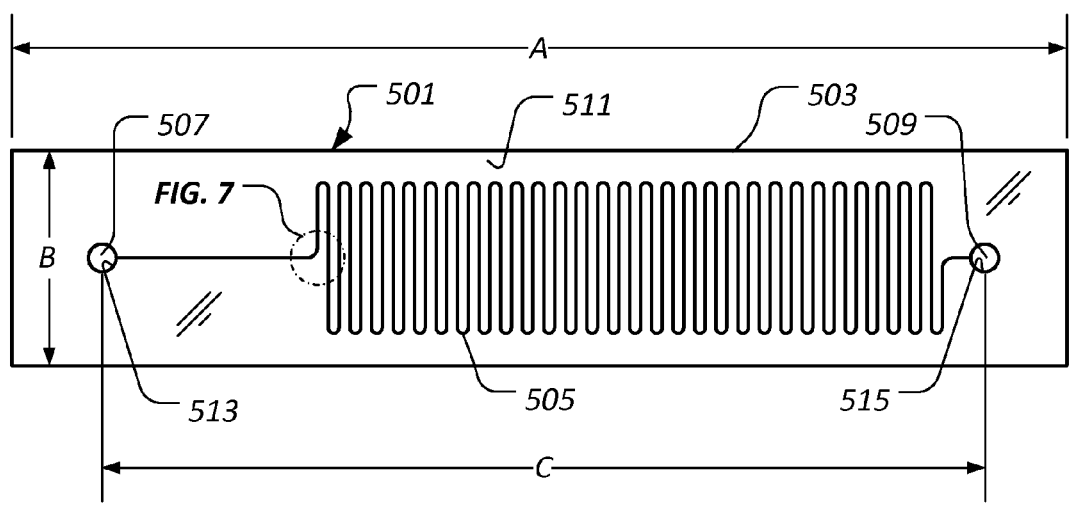
FIG. 5 is a top, plan view of a second illustrative embodiment of a microfluidic device for measuring thermo-physical properties of a reservoir fluid.
Figure 6:
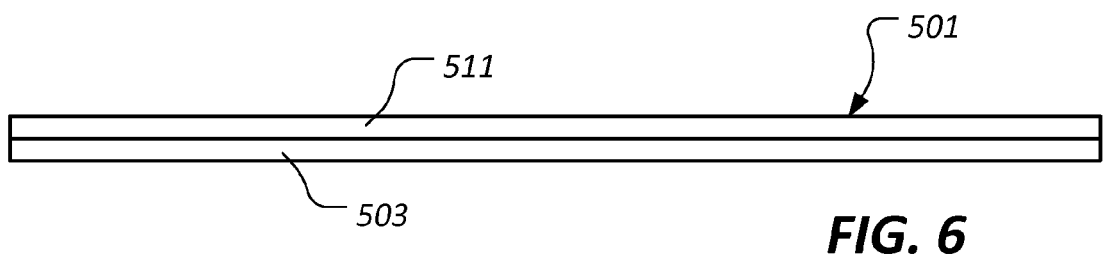
FIG. 6 is a side, elevational view of the microfluidic device of FIG. 5.

FIGS. 5 and 6 depict a second illustrative embodiment of a microfluidic device 501. As in microfluidic device 101 of FIG. 1, microfluidic device 501 comprises a first substrate 503 defining a microchannel 505, an entrance well 507, and an exit well 509. Microchannel 505 extends between and is in fluid communication with entrance well 507 and exit well 509. In the illustrated embodiment, first substrate 503 is made from silicon; however, first substrate 503 may be made from glass. Microchannel 505, entrance well 507, and exit well 509 are, in one embodiment, first patterned onto first substrate 503 using a photolithography technique and then etched into first substrate 503 using a deep reactive ion etching technique. As in the first embodiment shown in FIG. 1, in a preferred embodiment, microchannel 505 exhibits a length of one or more meters, a width of about 100 micrometers, and a depth of about 50 micrometers, although the present invention also contemplates other dimensions for microchannel 505.

Microfluidic device 501 further comprises a second substrate 511 defining an entrance passageway 513 and an exit passageway 515 in fluid communication with entrance well 507 and exit well 509. Second substrate 511 is made from glass, as discussed herein concerning second substrate 111 (shown in FIG. 1). In one embodiment, entrance passageway 513 and exit passageway 515 are generated in second substrate 511 using a water jet or abrasive water jet technique. First substrate 503 and second substrate 511 are preferably fused using an anodic bonding method after careful cleaning of the bonding surfaces of substrates 503 and 511.

The present invention contemplates microfluidic device 501 having any suitable size and/or shape needed for a particular implementation. In one embodiment, microfluidic device 501 exhibits an overall length A of about 80 millimeters and an overall width B of about 15 millimeters. In such an embodiment, passageways 513 and 515 are spaced apart a distance C of about 72 millimeters. It should be noted that microfluidic device 101 may also exhibit dimensions corresponding to microfluidic device 501. However, the scope of the present invention is not so limited.

Figure 8:
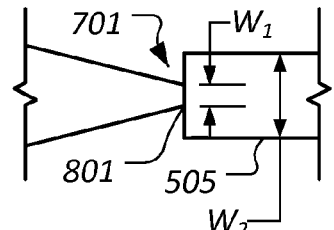
FIGS. 7-9 depict exemplary microchannel constrictions of the microfluidic device of FIG. 5.
Figure 7:
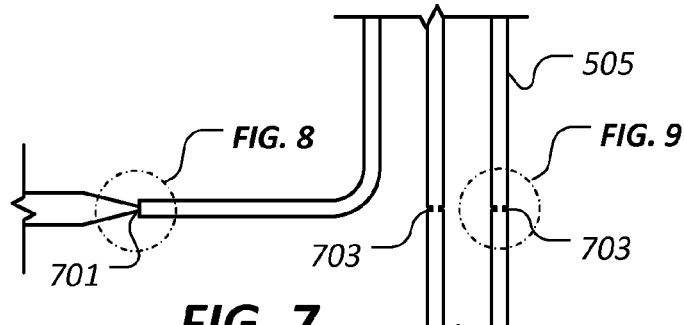
Figure 9:
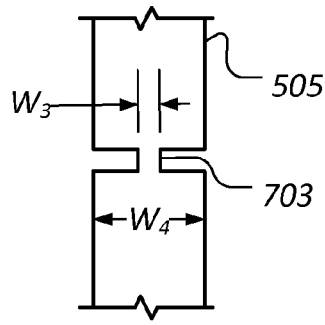

Referring to FIG. 7, one or more portions of microchannel 505 include zones of reduced cross-sectional area to induce the formation of bubble nuclei in the reservoir fluid. For example, as shown in FIGS. 7 and 8, a micro-venturi 701 is incorporated into an inlet of microchannel 505. Micro-venturi 701 includes a nozzle opening 801 having a width $W_1$, which is smaller than a width $W_2$ of microchannel 505. The contraction provided by micro-venturi 701 causes a substantial pressure drop in the reservoir fluid at nozzle opening 801 along with an increased velocity of reservoir fluid flow. The combined effect of the pressure drop and the increased velocity induces formation of bubble nuclei in the reservoir fluid. Preferably, microchannel 505 further includes one or more additional constrictions 703, as shown in FIGS. 7 and 9. Constrictions 703 exhibit widths $W_3$, which are smaller than a width $W_4$ of microchannel 505. Preferably, width $W_1$ of nozzle opening 801 and widths $W_3$ of constrictions 703 are about 20 micrometers, whereas the preferred width $W_2$ and $W_4$ of microchannel 505 is 100 micrometers. These restrictions increase the velocity of the reservoir fluid by up to about 500 percent.

Figure 10:
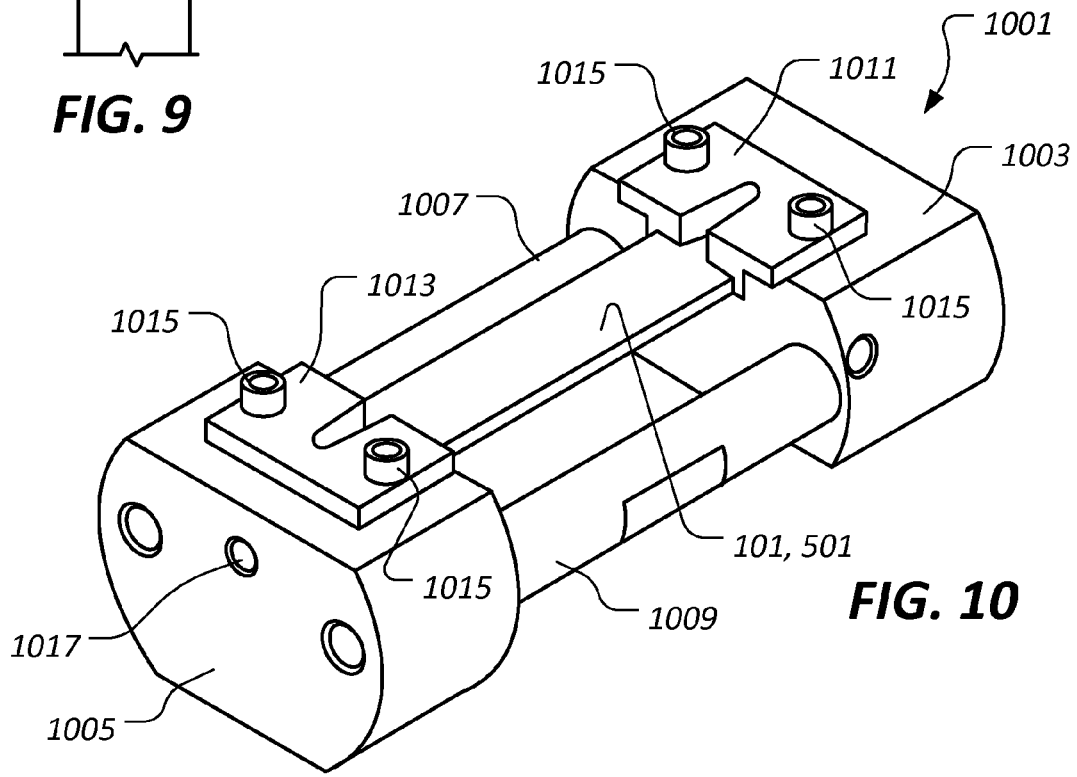
FIG. 10 depicts an illustrative embodiment of a microfluidic device holder in use holding a microfluidic device.

FIG. 10 depicts an illustrative embodiment of a microfluidic device holder 1001 in use holding a microfluidic device, such as microfluidic device 101 or 501. Holder 1001 comprises a first head 1003 and a second head 1005 connected by tie rods 1007 and 1009. Microfluidic device 101 or 501 is held in place on first head 1003 and second head 1005 by plates 1011 and 1013, respectively, which are attached to heads 1003 and 1005 by fasteners 1015. Holder 1001 provides a proper stand and a high pressure connection 1017 for transmitting the reservoir fluid to microfluidic device 101 or 501. Holder 1001 along with microfluidic device 101 or 501 can be placed on a microscope (not shown) or may be observed visually.

Figure 11:
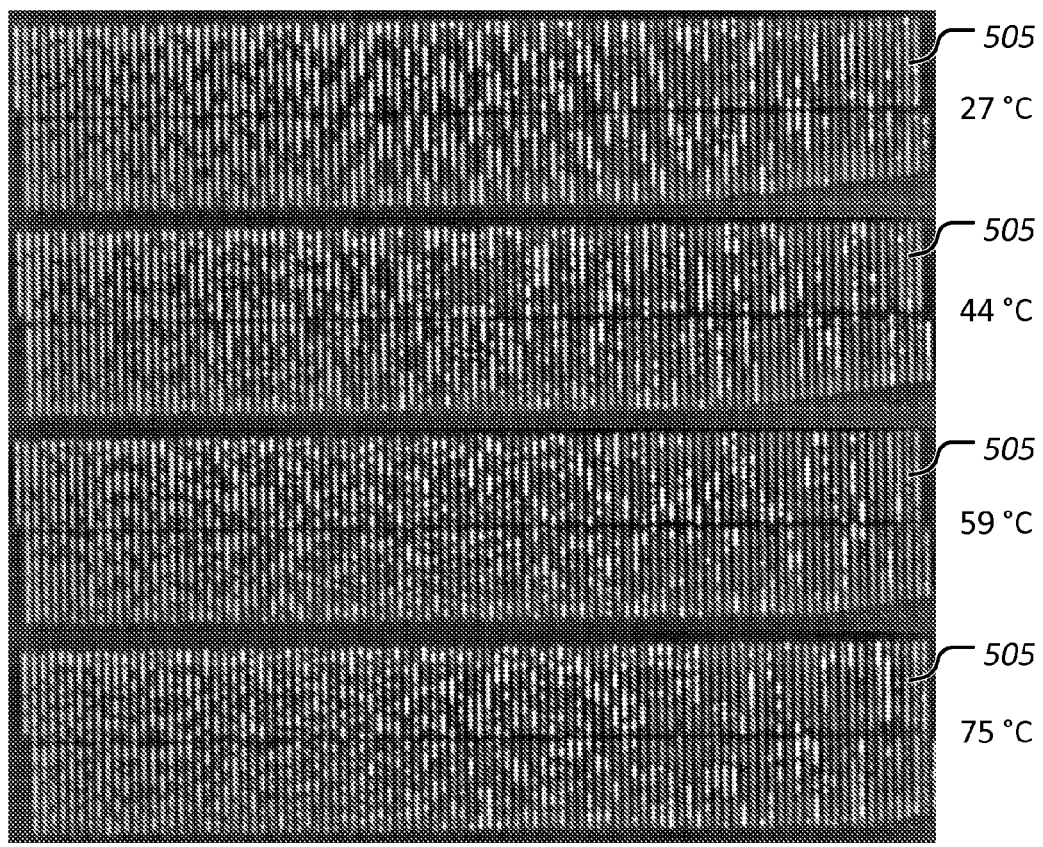
FIG. 11 provides a series of photographs depicting liquid/bubble distribution in an exemplary methane/decane fluid mixture in a microfluidic device.

FIG. 11 provides a series of photographs depicting liquid/bubble distributions at temperatures of 27° C., 44° C., 59° C., and 75° C. in an exemplary methane/decane fluid mixture disposed in microfluidic device 501. The fluid mixture is equilibrated at 37 kilograms/square centimeter (530 pounds/square inch) at room temperature. The injection pressure for each scenario is 42 kilograms/square centimeter (600 pounds/square inch). In FIG. 11, the fluid is injected into microfluidic device 501 from the left. In the photographs, the white lines depict slugs of liquid, whereas gas is shown as dark gaps separating the liquid slugs. The pressure of the fluid drops as the fluid moves downstream toward the exit. The pressure drop causes expansion of the gas bubbles along with more evaporation from the liquid phase, which is manifested by an increase in the void fraction, i.e., gas volume/total volume, in microchannel 505 (best shown in FIG. 5).

Figure 12:
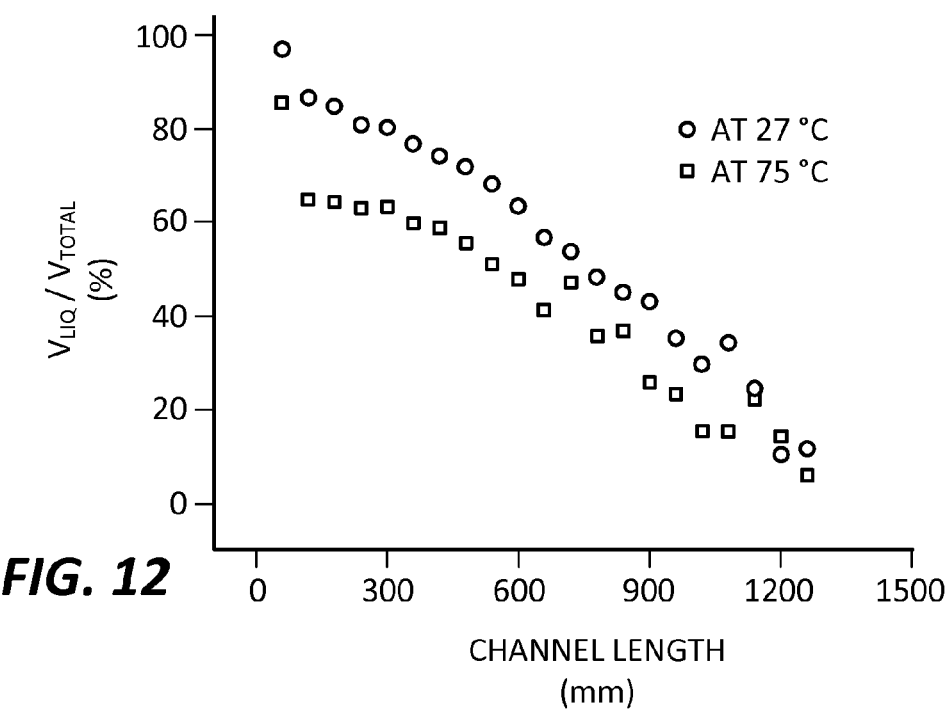
FIG. 12 is a graph representing the liquid volume as a percentage of total volume in an exemplary methane/decane fluid mixture due to the effect of temperature.
Figure 13:
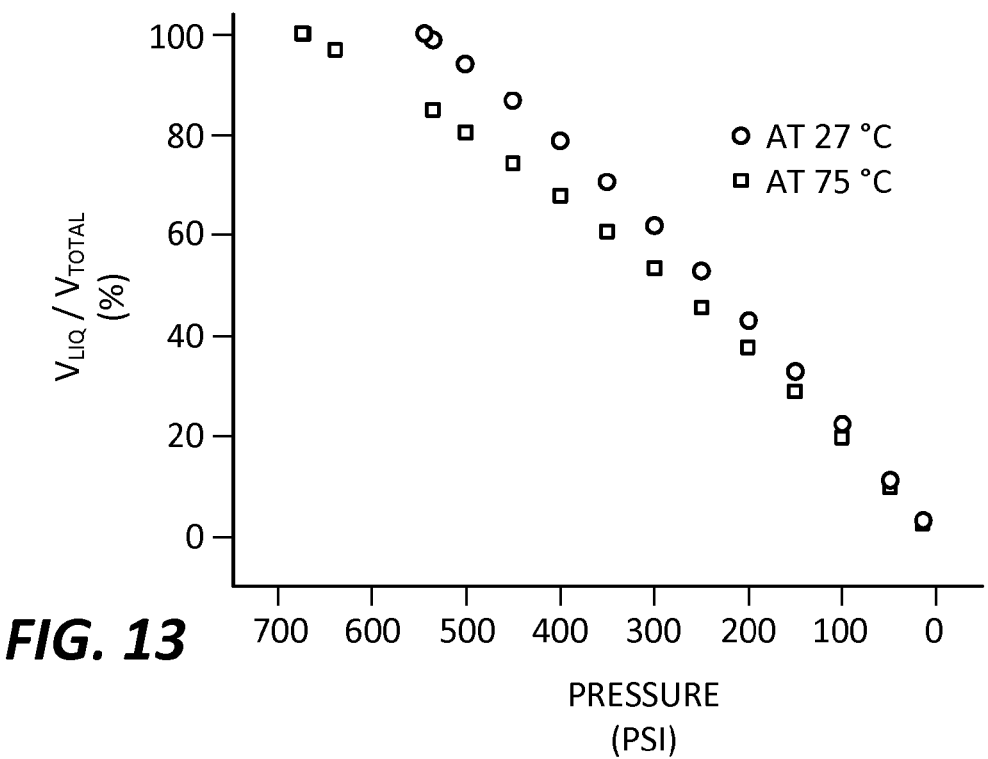
FIG. 13 is a graph representing conventional pressure-volume-temperature calculations for the methane/decane fluid mixture of FIG. 12.

FIG. 12 depicts the changes in the liquid volume as a percentage of total volume in an exemplary methane/decane fluid mixture having a 37 kilogram/square centimeter (530 pound/square inch) bubble point due to the effect of temperature. An increase in the temperature of microchannel 505 (best shown in FIG. 5) results in faster evaporation of the liquid and expansion of the gas. This is manifested by the measurements using image analysis techniques. These measurements are shown in FIG. 12 for temperatures of 27° C. and 75° C. In FIG. 12, the vertical axis represents the liquid volume as a percentage of total volume and the horizontal axis shows the length of microchannel 505. At 27° C., the volume of gas in the fluid is about three percent at the entrance of microchannel 505. The volume of gas increases to about 97 percent at atmospheric pressure near the exit of microchannel 505. At a temperature of 75° C., a trend similar to that found at 27° C. is observed. The gas volume, however, increases in the fluid at a greater rate. The results of these measurements are in accord with conventional pressure-volume-temperature calculations for this fluid, as shown in FIG. 13.

Using the data from FIG. 12, the necessary information for a typical constant composition expansion (CCE) experiment can be calculated. Furthermore, due to the short time required to achieve thermal equilibrium, the experiment can be performed at multiple temperatures, which results in more accurate phase behavior measurements.

Figure 14:
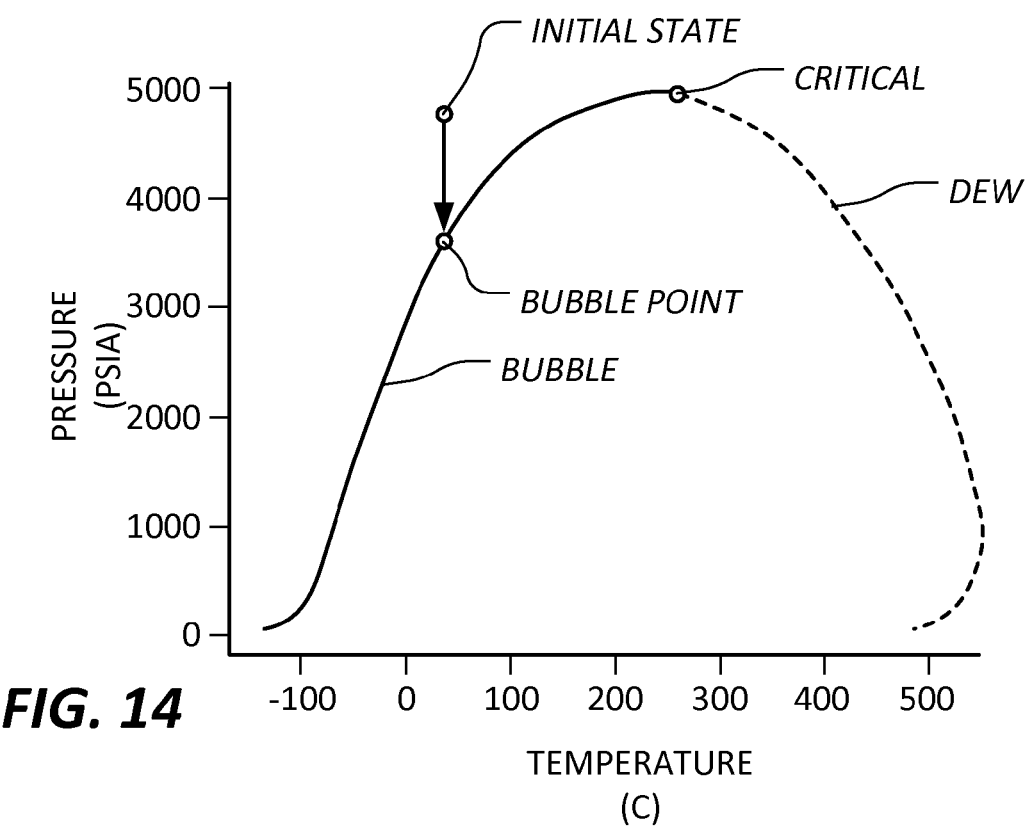
FIG. 14 is a graph depicting an exemplary phase envelope for a particular pressurized or "live" reservoir fluid.

FIG. 14 depicts an exemplary phase envelope for a particular pressurized or "live" reservoir fluid. At the downhole condition, the reservoir fluid is in an under-saturated state. In other words, the pressure of the reservoir is above the bubble point pressure. The arrow in FIG. 14 shows an isothermal pressure drop of the reservoir fluid to the bubble point. The bubble point represents a single point of the phase envelope. The measured bubble point using this technique is for a given temperature. The temperature of the reservoir fluid under experiment can be changed and the bubble point measured, which results in a reliable representation of the phase envelope.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope of the invention. Accordingly, the protection sought herein is as set forth in the claims below. Although the present invention is shown in a limited number of forms, it is not limited to just these forms, but is amenable to various changes and modifications.

What is claimed is:

1. A method for measuring thermo-physical properties of a reservoir fluid, the method comprising:
    providing a microfluidic device defining a fluid entrance, a fluid exit, and a microchannel extending between and in fluid communication with the fluid entrance and the fluid exit;
    introducing the reservoir fluid under pressure into the microchannel via the fluid entrance;
    establishing a stabilized flow of the reservoir fluid through the microchannel and from the fluid exit;
    inducing bubble formation in the reservoir fluid disposed in the microchannel; and
    determining one or more thermo-physical properties of the reservoir fluid based upon the size and concentration of the bubbles formed in the reservoir fluid disposed in the microchannel.

2. The method, according to claim 1, wherein determining the one or more thermo-physical properties is accomplished using images taken of the reservoir fluid disposed in the microchannel.

3. The method, according to claim 1, wherein the one or more thermo-physical properties includes one or more of a gas-oil-ratio, a phase envelope, and an equation of state.

4. The method, according to claim 1, wherein the bubble formation is induced by one or more zones of reduced cross-sectional area in the microchannel.

5. The method, according to claim 4, wherein the one or more zones of reduced cross-sectional area in the microchannel comprise a micro-venturi.

* * * * *